United States Patent [19]

Reuther et al.

[11] 4,324,550
[45] Apr. 13, 1982

[54] IMPLANT FOR THE JAW

[75] Inventors: Jürgen Reuther, Frankfurt, Fed. Rep. of Germany; Heinz Moser; Hermann Krauss, both of Selzach, Switzerland

[73] Assignee: Osteo AG, Selzach, Switzerland

[21] Appl. No.: 209,296

[22] Filed: Nov. 21, 1980

[30] Foreign Application Priority Data

Nov. 21, 1979 [CH] Switzerland .................. 10374/79

[51] Int. Cl.³ .............................................. A61C 8/00
[52] U.S. Cl. ..................................... 433/174; 433/169
[58] Field of Search ............... 433/174, 201, 168, 169, 433/170

[56] References Cited

U.S. PATENT DOCUMENTS 2,609,604  9/1952  Sprague ............................ 433/176
4,178,686 12/1979  Riess ................................. 433/173
4,185,383  1/1980  Heimke ............................ 433/173

FOREIGN PATENT DOCUMENTS 827689   9/1950  Fed. Rep. of Germany .
1721340  8/1955  Fed. Rep. of Germany .
2401323  7/1974  Fed. Rep. of Germany .
2413883  9/1975  Fed. Rep. of Germany .
1320655  6/1973  United Kingdom .
1352188  5/1974  United Kingdom .
1431563  4/1976  United Kingdom .

Primary Examiner—Robert Peshock
Attorney, Agent, or Firm—Wender, Murase & White

[57] ABSTRACT

An implant for the jaw includes an implant body, to be fixed without bone cement, a bed made of plastics material and an implant support for receiving the suprastructure. In order to reduce the specific load on the bone the implant body is provided with support ribs, which have the profile of a bone screw. The bed, providing a flexible layer between the implant body and support is frusto-conical towards its lower end and is spread by the implant support, when said support is screwed in.

This construction provides for secure anchorage of the implant body into the bone as well as of the bed and the implant support into the implant body.

9 Claims, 3 Drawing Figures

IMPLANT FOR THE JAW

BACKGROUND OF THE INVENTION

The present invention concerns an implant for the jaw, comprising an implant body for cementless implantation, a bed made of a plastics material and an implant support.

Implants for the jaw having two stabilisator wings at the implant body and an implant support which is fastened into a bed of plastics material are known. The wings confer to the implant body a rotational stability but they make more difficult exact adjustment and adaptation of the body, after the incision for the wings have been made. Furthermore, because the rest of the walls are smooth the adherence of the jaw-bone to said implant does not always follow. The bed of plastics material is necessary for obtaining a certain flexibility of the tooth and a dampening of the chewing load and is made as cylindrical casing with an exterior and internal thread.

BRIEF SUMMARY OF THE INVENTION

The present invention seeks to overcome these disadvantages by constructing an implant which provides better anchorage of the bone allows better adjustment by the implantation and has a bed with a stronger grip.

BRIEF DESCRIPTION OF THE DRAWING

The invention will be described further, by way of example, with reference to the accompanying drawings, in which.

DESCRIPTION OF THE PREFERRED EMBODIMENT

Figure 1:
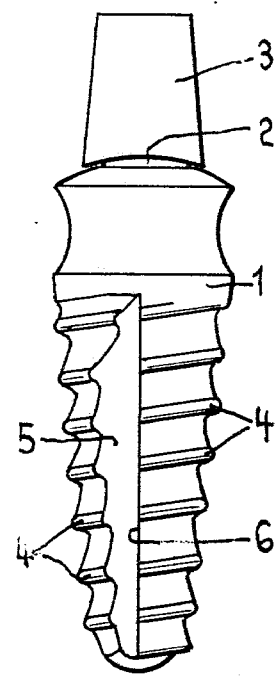
FIG. 1 is a side view of an implant according to the invention.
Figure 2:
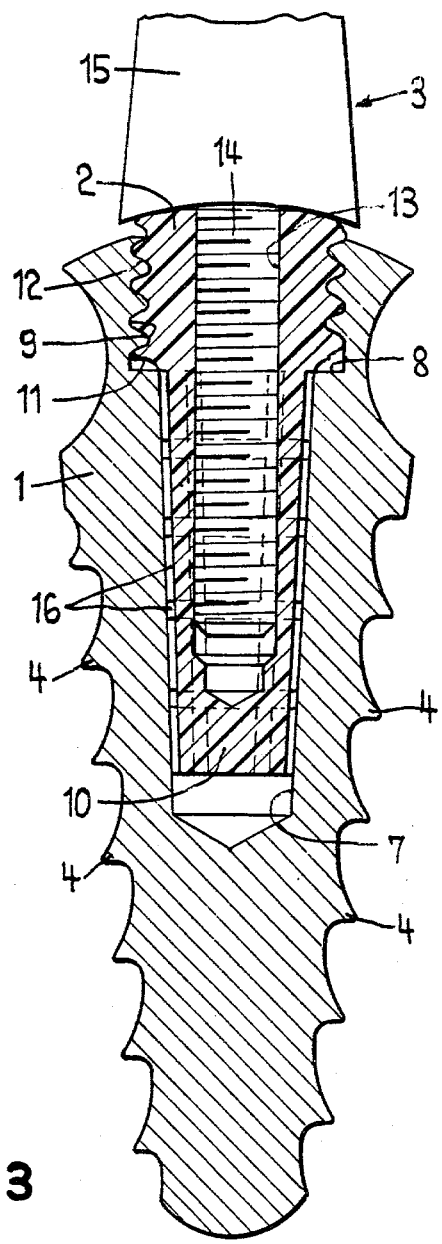
FIG. 2 is a sectional view in a larger scale of the implant of FIG. 1.
Figure 3:
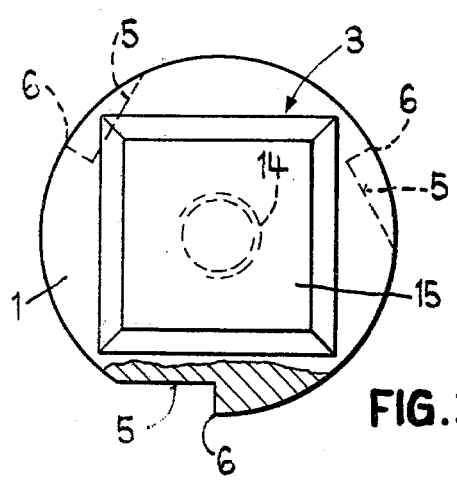
FIG. 3 is a top plan view of the implant of FIG. 2.

In sectional view in FIG. 2 is shown the implant body 1, the bed 2 made of plastics material and the implant support 3. The implant body 1, in this example made of aluminum-oxide ceramics, has a frusto-conical form towards the bottom reaching into the bone and includes support ribs 4 which have the profile of a bone screw. These support ribs decrease the specific load of the implant on the jaw-bone and simulate, therefore the anchorage of the bone at the implant. The ribs also provide further for the primary optical tight agglomeration of implant surface and surrounding bone. The surface of the implant body comprises three notches 5, see FIG. 3, which each having a cutting edge 6, facilitating the screwing in of the implant body. The implant body comprises further a conical hole 7, tapered towards the bottom, for receiving the bed 2. The conical hole 7 has at its top end a shoulder 8 opening into a cylindrical hole, which has a greater diameter and an internal thread 9. At the top, the hole is formed into a cross-slot, for the insertion of an appropriate tool.

The external form of the bed matches the two holes in the implant body and comprises a frusto-conical part 10, tapered towards the bottom, a shoulder 11 having an external thread 12. The bed 2 has an internal thread 13 for the fixation of the implant support 3. The outer surface of the bed, adjacent to the implant body, has a structure 16 for enabling a greater flexibility and deformability because the bed contacts the internal surface of the implant body only punctually. This structure allows also a dampening of the chewing forces on the bone.

The implant support 3 comprises a threaded stud 14 and a square head 15, tapered towards the top, for receiving the suprastructure, that is the tooth. The outer diameter of the stud is dimensioned such that the conical part 10 of a bed is spread when the support is screwed in, causing the wedging of the bed with the implant body. The implant support is made of an appropriate metal or metal alloy.

As to materials for the implant body 1, besides the already mentioned aluminiumoxide ceramics, all materials usually employed in the human medecine, as for example titanium, a chrome-cobalt-molybdenum-alloy, carbon-fibres reinforced polyethylene, stainless steel or carbon, can be employed whereas the bed can be made of polyethylene.

For implanting, a core hole with an appropriate diameter is drilled first, then a thread is turned in and the implant body is screwed in during which the cutting edges 6 are reducing the force to be applied on the implant body. Upon cementless fastening of the implant body in this manner the plastics material bed and afterwards, thereafter the implant support are screwed in.

We claim:

1. An implant for the jaw, comprising:
   a conical implant body having support ribs provided on the external surface thereof and an internal passageway extending from the base of said implant body towards the vertex of said implant body;
   a conical bed of a plastics material having an internal passageway extending from the base of said bed towards the vertex of said bed, said bed positioned coaxially within said internal passageway of said implant body; and
   an implant support positioned coaxially within said internal passageway of said bed, whereby said implant support is maintained in the jaw by cementless implantation of said implant body into the jaw.

2. An implant according to claim 1, wherein the base of said bed has a cylindrical portion with a thread which matches a thread in said internal passageway of said implant body, said bed also having a shoulder formed at the junction of said cylindrical portion which matches a shoulder provided in the internal passageway of said implant body.

3. An implant according to claim 1, wherein said support ribs are arranged so as to form a bone screw.

4. An implant according to claim 1, wherein said internal passageway of said bed is provided with a thread and said implant support has a threaded stud having a larger diameter than the diameter of said thread, thereby resulting in a wedging effect between said implant support, said bed and said implant body when said stud is screwed into said internal passageway of said bed.

5. An implant according to claim 1, wherein the external said surface of said implant body is provided with notches having cutting edges to facilitate screwing of said implant body into the jaw.

6. An implant according to claim 1, wherein said implant body is made of aluminiumoxide ceramics.

7. An implant according to claim 1, wherein said implant body is made of titanium, a chrome-cobalt-molybdenum-alloy, stainless steel, carbon or carbon-fibres reinforced polyethylene.

8. An implant according to claim 1 wherein the external surface of said bed is provided with projections which contact the surface of said internal passageway of said implant body.

9. An implant according to claim 1, wherein said implant support further includes a tapered square head extending above the base of said implant body.

* * * * *